(12) United States Patent
Dubnack et al.

(10) Patent No.: US 6,749,603 B2
(45) Date of Patent: Jun. 15, 2004

(54) ELECTRICAL PROBE

(75) Inventors: Steffen Dubnack, Jena (DE); Dirk Preuss, Jena (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/933,857

(22) Filed: Aug. 20, 2001

(65) Prior Publication Data

US 2003/0036756 A1 Feb. 20, 2003

(30) Foreign Application Priority Data

Apr. 7, 2001 (DE) .......................... 101 18 464

(51) Int. Cl.⁷ ............................... A61B 18/18
(52) U.S. Cl. .................. 606/13; 606/41; 606/14; 606/15
(58) Field of Search ............... 606/4, 5, 14, 15, 606/41; 607/88, 89

(56) References Cited

U.S. PATENT DOCUMENTS

| | | | | |
|---|---|---|---|---|
| 5,425,730 A | * | 6/1995 | Luloh | 606/15 |
| 5,509,916 A | * | 4/1996 | Taylor | 606/13 |
| 5,947,958 A | * | 9/1999 | Woodard et al. | 606/15 |
| 5,957,917 A | * | 9/1999 | Doiron et al. | 606/15 |
| 5,972,416 A | * | 10/1999 | Reimels et al. | 427/2.12 |
| 6,135,998 A | * | 10/2000 | Palanker | 606/39 |
| 6,164,280 A | * | 12/2000 | Everett et al. | 128/898 |
| 6,494,899 B1 | * | 12/2002 | Griffin et al. | 607/88 |

* cited by examiner

Primary Examiner—Roy D. Gibson
Assistant Examiner—Aaron Roane
(74) Attorney, Agent, or Firm—Reed Smith LLP

(57) ABSTRACT

An electrical probe which can be used in electrosurgery as well as for measurements is disclosed. The probe comprises an inner electrode and an outer electrode which are constructed coaxially. The isolator located between the electrodes is constructed as a light guide and can accordingly be utilized for illumination or irradiation by means of a laser.

17 Claims, 3 Drawing Sheets

ELECTRICAL PROBE

BACKGROUND OF THE INVENTION

This application claims priority of German Application No. 101 18 464 6 filed Apr. 7, 2001, the complete disclosures of which is hereby incorporated by reference.

a) Field of the Invention

The invention is directed to an electrical probe. A probe of this kind can preferably be used in ophthalmological surgery for electrosurgical cutting, ablation or coagulation of tissue.

b) Description of the Related Art

The use of electrosurgical procedures in ophthalmology is known per se and is disclosed, for example, in U.S. Pat. Nos. 6,135,998 and 5,755,716. U.S. Pat. No. 6,135,998 describes a probe in which an outer electrode is constructed coaxially around an inner wire-shaped electrode. The space between the electrodes is filled with an insulating material, e.g., also glass or fused silica.

Further, combined probes used for electrosurgical operation and laser operation are also known from general surgery (e.g., U.S. Pat. Nos. 5,011,483 and 5,509,916). In these cases, the laser light of correspondingly high-power lasers is guided in the vicinity of the ends of the electrodes of the electrosurgical probe by means of separate light-conducting fibers in order to treat the tissue with laser radiation as needed.

In operative use of an electrosurgical probe in ophthalmology, ensuring sufficient illumination of the interior of the eye and the fundus oculi is problematic. Therefore, illumination which is supplied via a second incision is often used in addition to the surgical tool. This additionally complicates performance of the operation and considerably increases stress and risk for the patient.

OBJECT AND SUMMARY OF THE INVENTION

Therefore, it is the primary object of the invention to provide a novel probe which makes the use of the probe more economical and improves the illumination conditions at the working location of the probe.

According to the invention, this object is met in an electrosurgical probe comprising a first electrode, a second electrode arranged coaxial to the first electrode and an isolator located between the electrodes. The isolator is constructed as a light guide. By light guides is meant in the following also optical waveguides which are suitable for components of the spectrum other than visible components. In this respect, it is advantageous to connect the light guides in an optically active manner with a light generating unit. This light generating unit can be a suitable lamp, e.g., a halogen lamp, as well as a laser. The radiation is advantageously coupled into the light guide by suitable optical systems, e.g., lenses or optical gratings, known to the person skilled in the art. According to the invention, the light guide can also comprise a bundle of light-conducting fibers. The electrodes have corresponding contacts for connecting to a power supply unit. It is particularly advantageous when the light guide comprises a flexible light guide which is constructed continuously from the probe tip to the light generating unit. Alternatively, the invention can also be realized in that the probe is constructed as a separable unit which is connected with the light generating unit via a flexible light guide with corresponding coupling points.

The light can be conducted in the light guide by the principle of total reflection. Alternatively, it may also be favorable to provide the jacket surfaces of the light guide with a reflective coating.

It has proven advantageous when the electrodes do not closely contact the insulator, but rather have a clearance of several hundredths of a millimeter. This increases the flexibility of the light guide; moreover, it has been shown that there is less light loss as a result of this step.

In realizing the invention, it has turned out that the probe according to the invention can also be used advantageously in other areas of technology. Its use is particularly advantageous when the measurements or treatments to be carried out require the combination of optical and electrical methods. For example, in cell biology, electric potentials or changes in potential are measured directly at the location of optical stimulation. For this purpose, light of suitable intensity, wavelength and/or signal duration is directed via the light guide to the relevant location on the specimen and simultaneously or subsequently detects a possible change in potential by means of the electrodes using measurement techniques. It is likewise possible to carry out electrical and optical stimulation simultaneously or with a delay in time in that the electrodes are acted upon by voltage and corresponding light pulses are directed via the light guide to the active point of the electrodes or into the vicinity thereof.

DESCRIPTION OF THE PREFERRED EMBODIMENTS

The invention will be described more fully in the following with reference to two preferred embodiment examples.

Figure 1:
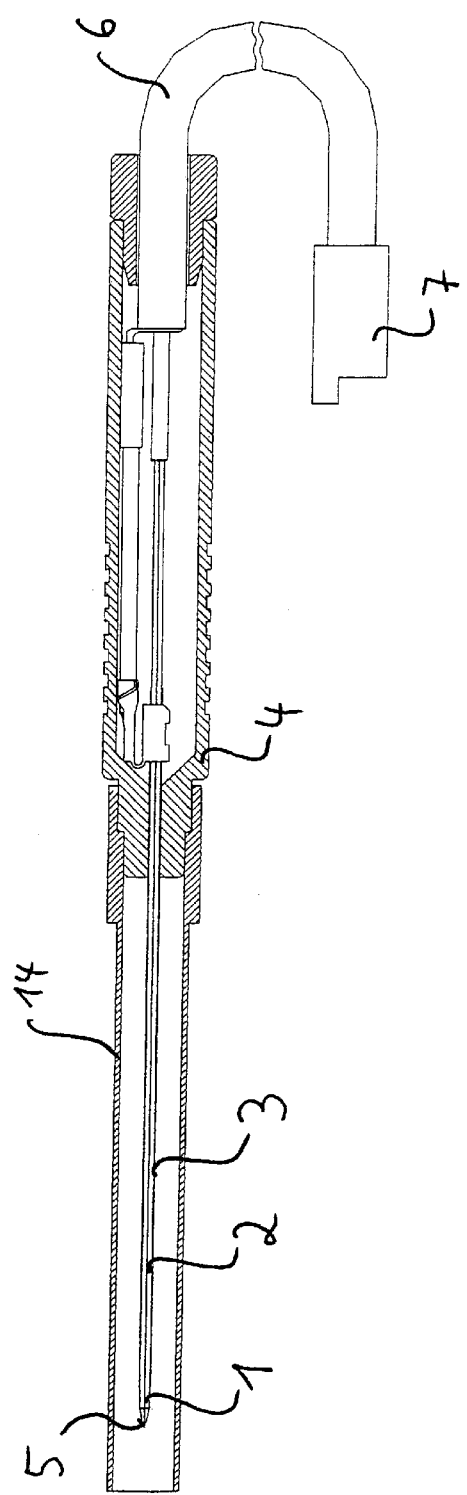
FIG. 1 is a partly sectional side view of the inventive light guide constructed continuously from the probe to a power supply/light generating unit.

FIG. 1 shows an implementation of the invention in which the light guide is constructed continuously from the probe to a power supply/light generating unit. The probe comprises an inner electrode 1 which is enclosed coaxially by a flexible light guide 2 and an outer electrode 3 which at least partially envelopes the light guide. The light guide comprises a suitable high-index, flexible, insulating material such as PMMA, but can also be constructed as gradient fiber. The light conduction is realized in a known manner by total internal reflection of the light at the interfaces of the fibers. An insulating handle 4 which partially surrounds the outer electrode 3 is used for stabilizing and handling the probe. The light guide 2 tapers to a point 5. The inner electrode 1 can terminate at the point 5 of the light guide 2 or can project beyond the latter by a small distance. The outer electrode 3 ends at a certain distance before the inner electrode exits from the light guide acting as an isolator. The outer electrode is surrounded by another isolator 6 between the handle and supply unit. The outer electrode is surrounded by another isolator 6 between the handle and supply unit. A connector 7 in which the inner electrode 1, outer electrode 3 and light guide 2 are guided out to separate connections is used to connect to the power supply unit. The inner electrode is guided at the end face of the light guide transverse to the side and to a contact. This has been shown to result in only a negligible reduction in the in-coupling efficiency of the light in the light guide. A protective cap 14 serves only to protect the probe during transport; it is removed before using the probe. The following dimensions were realized in a preferred embodiment form for ophthalmological surgery:

inner electrode 1: Ø0.010 . . . 0.1 mm light guide 2: Ø0.7 . . . 0.75 mm outer diameter of probe: 0.9 mm However, when used as a measurement probe, other dimensional ratios can also be realized. For purposes of deliberate influencing of a specimen with laser light, it is better not to let the light guide taper to a point, but to provide a smooth termination of the light-conducting fiber, beyond which the inner electrode projects by some hundredths or tenths of a millimeter.

Figure 2:
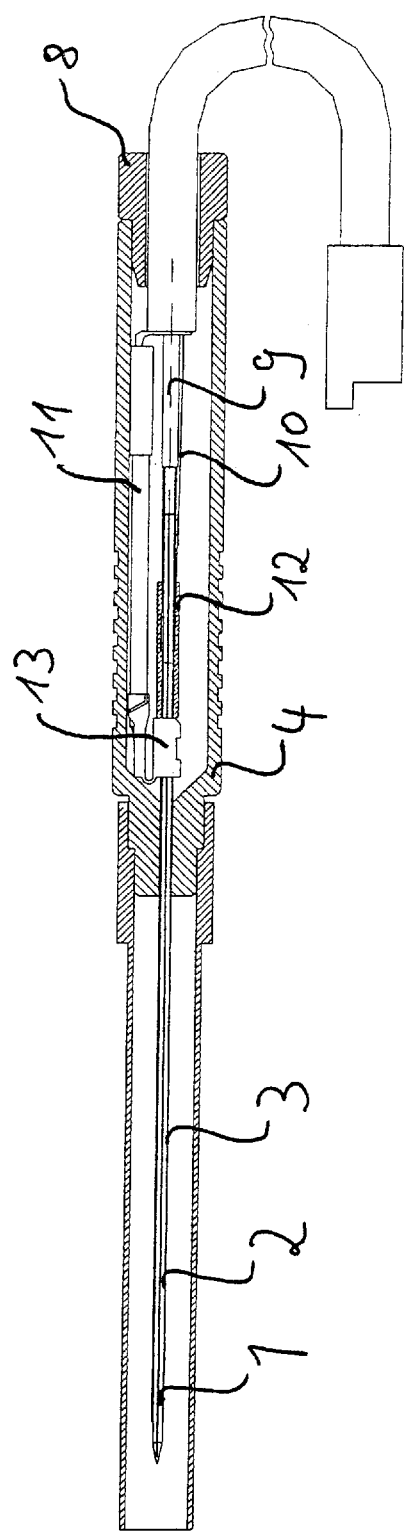
FIG. 2 shows a partly sectional side view of an assembled probe.

FIG. 2 shows an assembled probe. The probe likewise comprises an inner electrode 1 which is surrounded coaxially by a light guide 2 and an outer electrode 3 which at least partially surrounds the light guide. Aside from suitable plastics, glass or fused silica can also be considered for light guides.

The electrodes 1 and 3 and the light guide 2 are held by an insulating handle 4. A connection piece 8 by which the probe is connected with a light/power generating unit, not shown, via a flexible light guide 9 and power supply cables 10, 11 of the two electrodes 1 and 2 engages in the handle 4. The connection between the power supply cables 10, 11 and the electrodes 1, 3 is effected via corresponding contacts 12, 13. In the simplest case, the light from the flexible light guide 9 can be coupled into the light guide 2 of the probe, as is shown, by joining the ends of the two light guides; it is equally possible to provide a corresponding optical imaging system in this case.

Figure 3:
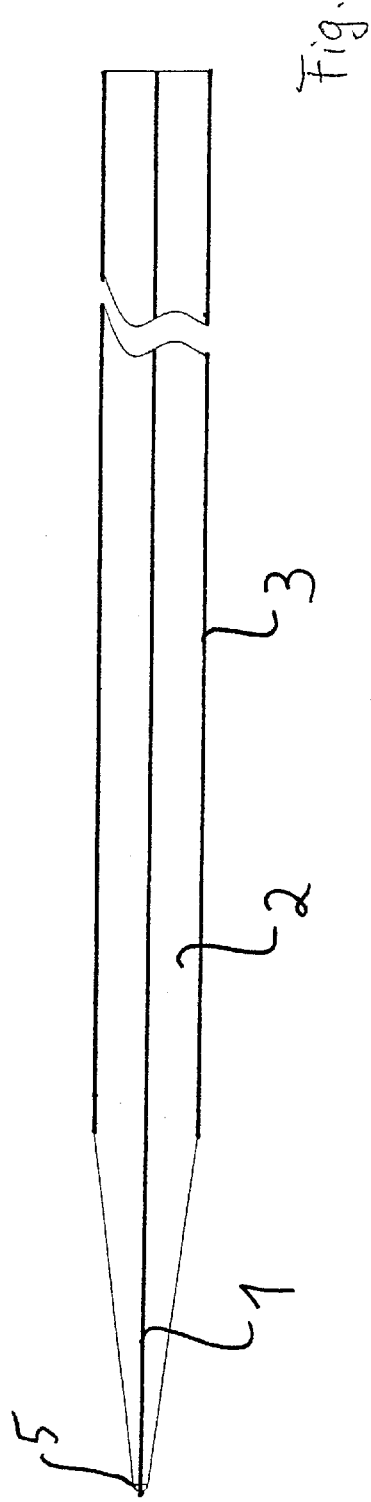
Figure 4:
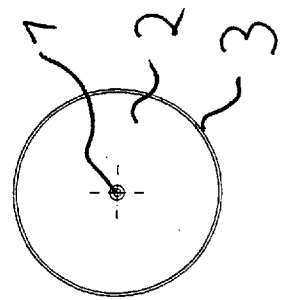

For purposes of illustration, an enlarged view of the probe tip is shown in FIG. 3 and a section through the probe according to the invention is shown in FIG. 4. The inner electrode 1 is surrounded coaxially by the insulating light guide 2 which is surrounded by the outer electrode 3. The light guide 2 terminates in a tip 5 and the inner electrode 1 projects beyond the tip 5 by a small distance.

With regard to the handling of the probe, the probe tip is advanced to the location of the intended action upon the tissue. Light is guided through the light guide 2 and is radiated diffusely or directly from the tip 5 so that the area surrounding the probe tip is illuminated. Observation can be carried out, for example, by means of an operation microscope. A halogen lamp or other suitable lighting can be used as light source. The relevant tissue can now be treated in a known manner by applying electrical pulses of suitable shape and intensity to the electrodes. Suitable electrical parameters are described in detail in U.S. Pat. No. 6,135,998.

It is also possible to replace the second electrode by a separate ground line which is connected to the patient at a suitable location. In this way, the probe according to the invention is simplified to form a monopolar probe, as it is called.

The realization of the invention is not restricted to the embodiment examples shown herein; in particular, other geometric dimensions can also be provided or the insulator can also be used for the transmission of other optical radiation in the ultraviolet or infrared spectral range.

While the foregoing description and drawings represent the present invention, it will be obvious to those skilled in the art that various changes may be made therein without departing from the true spirit and scope of the present invention.

What is claimed is:

1. An electrosurgical probe, for use in ophthalmological surgery, comprising:

a first electrode;

a second electrode, said second electrode being arranged coaxial to the first electrode; and an isolator located between the electrodes, said isolator being constructed as a light guide.

2. The electrosurgical probe according to claim 1, wherein the light guide is connected in optically active manner with a light generating unit.

3. The electrosurgical probe according to claim 2, wherein the light generating unit comprises a halogen lamp with an optical system for coupling light into the light guide.

4. The electrosurgical probe according to claim 2, wherein the light generating unit comprises a laser.

5. The electrosurgical probe according to claim 2, wherein the light guide is constructed at least partially as a flexible light guide, and wherein the flexible light guide is connected with the light generating unit.

6. The electrosurgical probe according to claim 2, wherein the probe is constructed as a combined probe, wherein the light guide is connected, via an in-coupling location, to a second light guide which is flexible, and wherein the flexible light guide is connected with the light generating unit.

7. The electrosurgical probe according to claim 1, wherein the electrodes have contacts for connecting to a power supply unit.

8. The electrosurgical probe according to claim 1, wherein the light guide comprises individual light guide fibers.

9. An electrical probe comprising:

a first electrode;

a second electrode, said second electrode being arranged coaxial to said first electrode which is an inner electrode; and an isolator located between the electrodes, wherein the isolator is constructed as a light guide.

10. The electrical probe according to claim 9, wherein the light guide is connected in optically active manner with a light generating unit.

11. The electrical probe according to claim 10, wherein the light generating unit comprises a halogen lamp with an optical system for coupling light into the light guide.

12. The electrical probe according to claim 10, wherein the light generating unit comprises a laser.

13. The electrical probe according to claim 10, wherein the light guide is constructed as a flexible light guide, and wherein the flexible light guide is connected with the light generating unit.

14. The electrical probe according to claim 10, wherein the probe is constructed as an offset probe, wherein the light guide is connected, via an in-coupling location, to a flexible light guide, and wherein the flexible light guide is connected to the light generating unit.

15. The electrical probe according to claim 9, wherein the electrodes have contacts for connecting to a power supply unit.

16. The electrical probe according to claim 9, wherein the light guide comprises individual light guide fibers.

17. The electrical probe according to claim 9, wherein the electrodes have contacts for connecting to a current-measuring and/or voltage-measuring device.

* * * * *